United States Patent [19]
Chandy et al.

[11] Patent Number: 5,559,009
[45] Date of Patent: Sep. 24, 1996

[54] VOLTAGE-GATED POTASSIUM CHANNEL GENE, KV1.7, VECTORS AND HOST CELLS COMPRISING THE SAME, AND RECOMBINANT METHODS OF MAKING POTASSIUM CHANNEL PROTEINS

[75] Inventors: Kanianthara G. Chandy, Laguna Beach; Katalin Kalman; Grischa Chandy, both of Irvine; George A. Gutman, Costa Mesa, all of Calif.

[73] Assignee: The Regents of The University of California, Oakland, Calif.

[21] Appl. No.: 288,405

[22] Filed: Aug. 10, 1994

Related U.S. Application Data

[63] Continuation-in-part of Ser. No. 207,401, Mar. 4, 1994, abandoned.

[51] Int. Cl.$^6$ ............... C12N 15/12; C12N 15/63; C12N 5/10; C12N 1/21
[52] U.S. Cl. ............... 435/69.1; 536/23.5; 435/320.1; 435/240.2; 435/252.3; 435/254.11
[58] Field of Search ............... 536/23.5; 435/69.1, 435/320.1, 240.2, 252.3, 254.11

[56] References Cited

PUBLICATIONS

Bell, G. I., et al., "Sequence of the Human Insulin Gene", *Nature*, 284:26–32, (1980).
Horst–Sikorska, W., et al., "Prevalence of beta allele of the insulin gene in type II diabetes mellitus", *Human Genetics*, 93:325–328, (1994).
Herman, W. H., et al., "Abnormal Insulin Secretion, Not Insulin Resistance, Is the Genetic or Primary Defect of MODY in the RW Pedigree", *Diabetes*, 43:40–46, (1994).
Boyd, III, A. E., "Sulfonylurea Receptors, Ion Channels, and Fruit Flies", *Diabetes*, 37:847–850, (1988).
Rajan, A. S., et al., "Ion Channels and Insulin Secretion", *Diabetes Care*, 13(3):340–363, (1990).
Misler, S., et al., "A Metabolite–regulated potassium channel in rat pancreatic B cells", *Proc. Nat'l. Acad. Sci.*, 83:7119–7123, (1986).
Petersen, O. H. et al., "Electrophysiology of the Pancreas", *Physiological Reviews*, 67(3):1054–1116, (1987).
Ashcroft, F. M., "Adenosine 5'-Triphosphate-Sensitive Potassium Channels", *Ann. Rev. Neurosci.*, 11:97–118, (1988).
Dukes, I., et al., "Dependence on NADH Produced during Glycolysis for β–Cell Glucose Signaling", *The Journal of Biological Chemistry*, 269(15):10979–10982, (1994).
Cook, D. L., et al., "Pancreatic B Cells are Bursting, but how?", *Trends Neurosci*, 14:411–414, (1991).
Smith, P. A., et al., "Delayed Rectifying and Calcium–activated K+ Channels and Their Significance for Action Potential Repolarization in Mouse pancreatic β–Cells", *J. Gen. Physiol.*, 95:1041–1059, (1990).
Smith, P. A., et al., "Simultaneous recordings of glucose dependent electrical activity and ATP–regulated K+–currents in isolated mouse pancreatic β–cells", *FEBS*, 261(1):187–190, (1990).
Atwater, I., et al., "Properties of the Ca–Activated K+ Channel in Pancreatic β–Cells", *Cell Calcium*, 4:451–461, (1983).
Ammala, C., et al., "Inositol trisphosphate–dependent periodic activation of a $Ca^{2+}$–activated $K^+$ conductance in glucose–stimulated pancreatic β–cells", *Nature*, 353:849–853, (1991).
Worley III, J. F., et al., "Endoplasmic Reticulum calcium Store Regulates Membrane Potential in Mouse Islet β–Cells", *The Journal of Biological Chemistry*, 269 (20):14359–14362, (1994).
Bertolli, A., et al. "Activation and Deactivation Properties of Rat Brain $K^+$ Channels of the Shaker–Related Subfamily," *European Biophysics Journal*, 23:379–384 (1994).
Betsholtz, C., et al., "Expression of voltage–gated $K^+$ Channels in Insulin–Producing Cells: Analysis by Polymerase Chain Reaction," *FEBS Letters*, 263(1):121–126 (1990).
Chandy, K. G., et al., "Nomenclature for Mammalian Potassium Channel Genes," *Trends in Pharmacological Sciences*, 14:434 (1993).
Philipson, L. H., et al., "Sequence and Functional Expression in *Xenopus oocytes* of a Human Insulinoma and Islet Potassium Channel," *Proc. Nat'l. Acad. of Sci. USA*, 88:53–57 (1991).

*Primary Examiner*—Garnette D. Draper
*Assistant Examiner*—David L. Fitzgerald
*Attorney, Agent, or Firm*—Walter H. Dreger

[57] ABSTRACT

This disclosure relates to the identification of a new voltage-gated potassium channel gene, Kv1.7, which is expressed in pancreatic β-cells. The invention utilizes this new potassium channel for assays designed to identify extrinsic materials with the ability to modulate said channel for the development of therapeutics effective in the treatment of non-insulin-dependent diabetes mellitus.

7 Claims, 6 Drawing Sheets

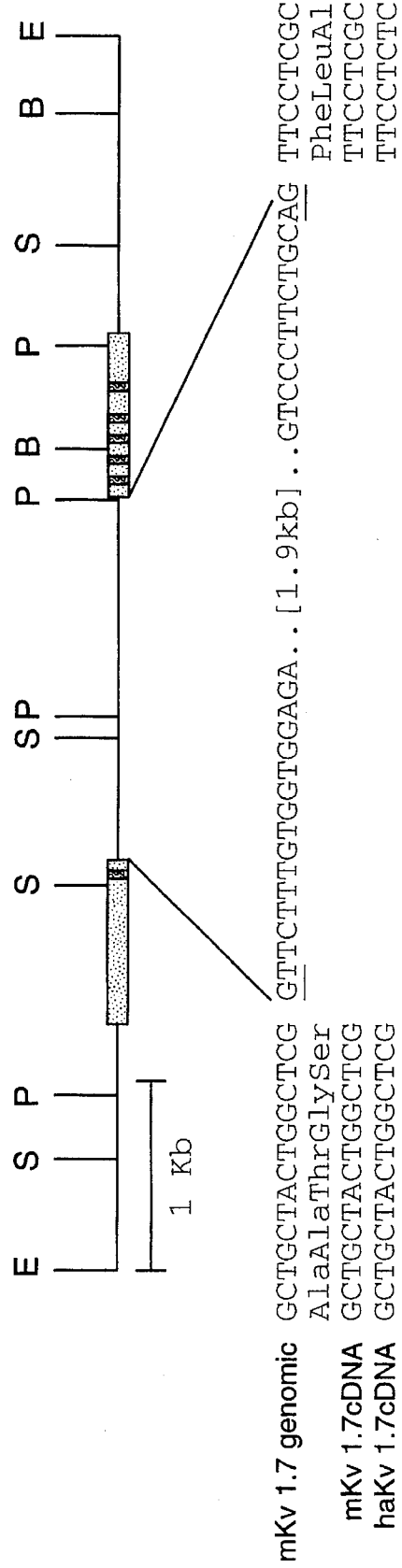
FIG._1A

```
MTTRESSRDPRKSAGWQCFHRCGTAEGAPSPAGVTPPPPPRPGRTFHAIFTRRHRTPDWGGCGVGATRPFTGRPGCARHG   80
                                                      ┌─TY─K─┐
ATVPAALRCCERLVLNVAGLRFETRARTLGRFPDTLLGDPVRRSRFYDGARAEYFFDRHRPSFDAVLYYQSGGRLRRPA  160
                                                          ────────S1────────
HVPLDVFLEEVSFYGLGRRLARLREDEGCAVAERPLPPFARQLWLLFEFPESSQAARVLAVVSVLVLVSIVVFCLETL  240
──────                                                    ─────────S2──────
                     *                                       ┌─PKC┐
PDFRDDRDDPGLAPVAAATGSFLARLNGSSPMPGAPPRQPFNDPFFVVETLCICWFSFELLVRLVACPSKAVFFKNVMNL  320
                                          ────────S4─────        ───────S5═══
══════S3══════                                                         ┌─P─┐
IDFVAILPYFVALGTELARQRGVGQPAMSLAILRVIRLVRFIFKLSRHSKGLQILGQTLRASMRELGLLISFLFIGVV  400
                                                       ──────S6──────
LFSSAVYFAEVDRVDTHFTSIPESFWWAVVTMTTVGYGDMAPVTVGGKIVGSLCAIAGVLTISLPVPVIVSNFSYFYHRE  480

TEGEEEAGMYSHVDTQPCGTLEGKANGGLVDSEVPELLPPLWPPAGKHMVTEV                             532
```

*FIG._1B*

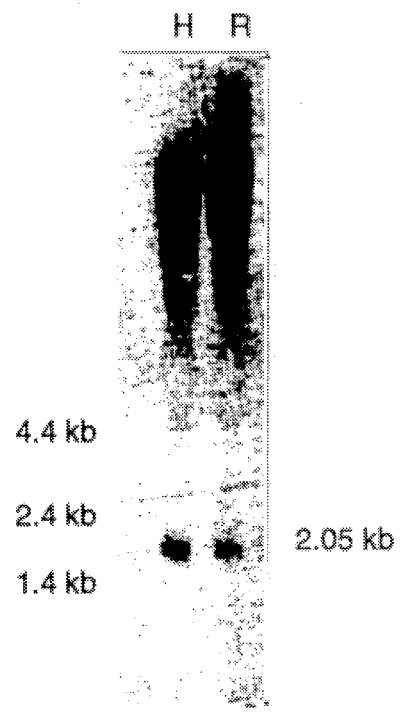
FIG._2
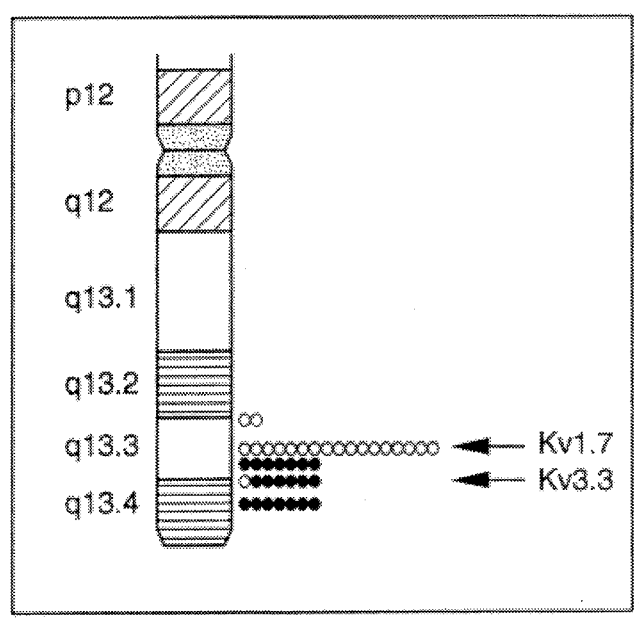
FIG._4

```
ATGACTACAAGGGAAAGCTCAAGAGATCCACGGAAAAGCCCGGGTGGCAGTGTTCCAC           60
AGGTGTGGAACGGCAGAGGGCGCCCCTAGCCCCGGGGGTAACACCGCCCCCCCG              120
                                         - - - -       -G- -GG-
CGCCCTGGCCGGACTTTCCATGCTATTTTACCCGCCGGACACCCGGACACCCGACTGGGGT       180
                                       - -GN- -G- - - - - -TA- - -
GGCTGCGGGCGTCGGGGCCACACGTCCGTTCACCCGGTCGCCCGGGCTGTGCGCGCCATGGA      240
- - - - -G- - - - - -G- -N- -G
GCCACGGTGCCCGCCCCTGCGCTGCGAGCGGCTGGTGCTCAACGTGGCCGGGTTG             300
CGCTTCGAGACCCGCGCTTCTACGACGGCGCGCCGAGTATTTCTTCGACCAGACCCG           360
GTGCGCCGCAGCCGCTTCTACGACGGCGCGCCGAGTATTTCTTCGACCGACACCGG            420
CCCAGCTTCGATGCGGTGCTCTACTACCAGTCGGGGCTGAGACGGGCCGGGCG               480
CACGTGCCCCTCGACGTCTTCCTGGAGGAGTGTCCTTCTACGGGCGCTGGGGCGGGGCTG        540
GCGCGGGCTGCGGGAGGACGAGGGCTGCGCTGCGAGCGGCCGCTGCCCCCGCCCTTT           600
GCGCGTCAGCTCTGCTCTTCGAATTCCCTGAGAGCTCGCAGGCTGCGCGTGCTC              660
                                                          - - - -
GCC GTGGTCTCCGTACTCGTCATCCTGGTCTCCATCGTGGTCTTTGCCTCGAGACACTG        720
 -T-C- -A- - - - - -G- - - - -C- - - - - -C- - - - - - - - - -G- -
```

FIG._3A

```
CCAGACTTCCGCGACGACCGCGATGACCCGGGGCTCCGCGGTAGCGGCTGCTACTGGC      780
--T------

TCGTTCCTCGCTCGGCTCAATGGCTCC AGTCCCATGCCAGGAGCCCCGACAGCCC       840
--CGA------G------------    --C--C- AN-

TTCAACGATCCATTCTTTGTGGTGGAGACCCTGTATCTGCTGGTTCTCCTTTGAGC TG     900
-------------------------------------AC-TT---  ---------A--

CTGGTGCATCTGGTGGCCTGCCCTAGCAAAGCTGTGTTCTTCAAGAATGTGATGAACCTA    960
------G----C--G--T--A----------------A--T-----------------T

ATTGACTTCGTGGCCATCCTGCCTTACTTCGTGGCCCTGGGCACGGAGTTAGCCCGGCAG    1020
------------------------------------T--------A---------T---

CGGGGTGTGGGCCAGCCGGCTATGTCCCTGGCCATCCTAAGG GTCATCCGATTGGTGCGT   1080
----C----------------A--------------------- G----A----N------A

GTCTTCCGCATCTTCAAGCTCTCCAGGCATTCGAAGGGTCTACAGATCTTGGGTCAG ACA   1140
------------N---N--N----N---------CN-G--A-------C---G--G

CTGCGGGCTTCCATGCGTGA GCTAGGTCTCCTCCTCATCTCCTCTTCCTCTTCATTGGCGTGGTC  1200
--T---C---------A---G--C-----------TT-----------C--T-----

CTCTTTTCCAGCGCAGTCTACTTTGCTGAAGTGGACCGGGTGGACACCCATTTCACCAGC   1260
---------

ATCCCGGAGTCCTTTTGGTGGGCAGTGGTCACCATGACCACGGTTGGCTATGGGGACATG   1320
```

FIG._3B

```
GCACCCGTCACCGTGGGCAAGATCGTGGGCTCTCTGTGTGCCATTGCAGGTGTGCTC         1380
ACCATCTCTCTGCCCTGTGCCTGTCATTGTCTCTAACTTTAGCTACTTTTACCACCGGGAG    1440
--T--C----A---C-----------------C--T--C---------T------------
ACAGAGGGGCGAAGAGGCAGGGATGTACAGCCATGTGGACACACAGCCCTGCGGTACCCTG    1500
-----------------------T-------T--------------TG-----T--T--CC-A---
GAGGG   CAAGGCTAAT   GGGGGGCTGGTGGACTCTGAGGTGCCTGAACTCCTCCCAC    1555
--N--NN-N-N--NNCCAAT-------------------------GGG----A-----G--A-CA--T-
CACTCTGGCCCCCTGCAGGAAACACATGGTGACTGAGGTGTGA (end)                1599
------G-A--CC--------------C----C---A-------GGAACAGTTGAGGTCTG
CAGGAATTCGATATCAAGCTTATCGATACCGT
```

FIG._3C

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 32 base pairs
        ( B ) TYPE: nucleic acid
        ( C ) STRANDEDNESS: double
        ( D ) TOPOLOGY: both ( i x ) FEATURE:
        ( A ) NAME/KEY: CDS
        ( B ) LOCATION: 1..15

( x i ) SEQUENCE DESCRIPTION: SEQ ID NO:1:

```
GCT  GCT  ACT  GGC  TCG  GTTCTTTGTG GTGGAGA              3 2
Ala  Ala  Thr  Gly  Ser
 1                   5
```

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Ala  Ala  Thr  Gly  Ser
 1                    5
```

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: double
        ( D ) TOPOLOGY: both ( i x ) FEATURE:
        ( A ) NAME/KEY: CDS
        ( B ) LOCATION: 14..25

( x i ) SEQUENCE DESCRIPTION: SEQ ID NO:3:

```
GTCCCTTCTG CAG  TTC  CTC  GCC  CGA                          2 5
           Phe  Leu  Ala  Arg
            1
```

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Phe  Leu  Ala  Arg
 1
```

( 2 ) INFORMATION FOR SEQ ID NO:5:

( i ) SEQUENCE CHARACTERISTICS:
        ( A ) LENGTH: 27 base pairs
        ( B ) TYPE: nucleic acid
        ( C ) STRANDEDNESS: double
        ( D ) TOPOLOGY: both ( i x ) FEATURE:
        ( A ) NAME/KEY: CDS
        ( B ) LOCATION: 1..27

( x i ) SEQUENCE DESCRIPTION: SEQ ID NO:5:

```
GCT  GCT  ACT  GGC  TCG  TTC  CTC  GCC  CGA                 2 7
Ala  Ala  Thr  Gly  Ser  Phe  Leu  Ala  Arg
 1                    5
```

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

Ala Ala Thr Gly Ser Phe Leu Ala Arg
1               5

( 2 ) INFORMATION FOR SEQ ID NO:7:

( i ) SEQUENCE CHARACTERISTICS:
        ( A ) LENGTH: 27 base pairs
        ( B ) TYPE: nucleic acid
        ( C ) STRANDEDNESS: double
        ( D ) TOPOLOGY: both ( i x ) FEATURE:
        ( A ) NAME/KEY: CDS
        ( B ) LOCATION: 1..27

( x i ) SEQUENCE DESCRIPTION: SEQ ID NO:7:

```
GCT GCT ACT GGC TCG TTC CTC TCT CGG                                           27
Ala Ala Thr Gly Ser Phe Leu Ser Arg
 1               5
```

( 2 ) INFORMATION FOR SEQ ID NO:8:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

Ala Ala Thr Gly Ser Phe Leu Ser Arg
 1               5

( 2 ) INFORMATION FOR SEQ ID NO:9:

( i ) SEQUENCE CHARACTERISTICS:
        ( A ) LENGTH: 1599 base pairs
        ( B ) TYPE: nucleic acid
        ( C ) STRANDEDNESS: double
        ( D ) TOPOLOGY: both ( i x ) FEATURE:
        ( A ) NAME/KEY: CDS
        ( B ) LOCATION: 1..1599

( x i ) SEQUENCE DESCRIPTION: SEQ ID NO:9:

```
ATG ACT ACA AGG GAA AGC TCA AGA GAT CCA CGG AAA AGC GCC GGG TGG              48
Met Thr Thr Arg Glu Ser Ser Arg Asp Pro Arg Lys Ser Ala Gly Trp
 1               5                  10                  15

CAG TGT TTC CAC AGG TGT GGA ACG GCA GAG GGC GCC CCT AGC CCC GCG              96
Gln Cys Phe His Arg Cys Gly Thr Ala Glu Gly Ala Pro Ser Pro Ala
                20                  25                  30

GGG GTA ACA CCG CCC CCT CCC CCG CGC CCT GGC CGG ACT TTC CAT GCT             144
Gly Val Thr Pro Pro Pro Pro Arg Pro Gly Arg Thr Phe His Ala
                35                  40                  45

ATT TTT ACC CGC CGA CAC CGG ACA CCC GAC TGG GGT GGC TGC GGC GTC             192
Ile Phe Thr Arg Arg His Arg Thr Pro Asp Trp Gly Gly Cys Gly Val
                50                  55                  60

GGG GCC ACA CGT CCG TTC ACC GGT CGC CCG GGC TGT GCG CGC CAT GGA             240
Gly Ala Thr Arg Pro Phe Thr Gly Arg Pro Gly Cys Ala Arg His Gly
 65                  70                  75                  80

GCC ACG GTG CCC GCC GCC CTG CGC TGC TGC GAG CGG CTG GTG CTC AAC             288
Ala Thr Val Pro Ala Ala Leu Arg Cys Cys Glu Arg Leu Val Leu Asn
                85                  90                  95

GTG GCC GGG TTG CGC TTC GAG ACC CGC GCG CGC ACG CTC GGC CGC TTC             336
Val Ala Gly Leu Arg Phe Glu Thr Arg Ala Arg Thr Leu Gly Arg Phe
                100                 105                 110
```

| | | | | | | | | | | | | | | | | |
|---|---|---|---|---|---|---|---|---|---|---|---|---|---|---|---|---|
| CCG | GAC | ACG | CTG | CTG | GGG | GAC | CCG | GTG | CGC | CGC | AGC | CGC | TTC | TAC | GAC | 384 |
| Pro | Asp | Thr 115 | Leu | Leu | Gly | Asp | Pro 120 | Val | Arg | Arg | Ser | Arg 125 | Phe | Tyr | Asp | |
| GGC | GCG | CGC | GCC | GAG | TAT | TTC | TTC | GAC | CGA | CAC | CGG | CCC | AGC | TTC | GAT | 432 |
| Gly | Ala | Arg 130 | Ala | Glu | Tyr | Phe | Phe 135 | Asp | Arg | His | Arg 140 | Pro | Ser | Phe | Asp | |
| GCG | GTG | CTC | TAC | TAC | TAC | CAG | TCG | GGC | GGC | CGG | CTG | AGA | CGG | CCG | GCG | 480 |
| Ala 145 | Val | Leu | Tyr | Tyr | Tyr 150 | Gln | Ser | Gly | Gly | Arg 155 | Leu | Arg | Arg | Pro | Ala 160 | |
| CAC | GTG | CCC | CTC | GAC | GTC | TTC | CTG | GAG | GAG | GTG | TCC | TTC | TAC | GGG | CTG | 528 |
| His | Val | Pro | Leu | Asp 165 | Val | Phe | Leu | Glu | Glu 170 | Val | Ser | Phe | Tyr | Gly 175 | Leu | |
| GGG | CGG | CGG | CTG | GCG | CGG | CTG | CGG | GAG | GAC | GAG | GGC | TGC | GCG | GTC | GCC | 576 |
| Gly | Arg | Arg | Leu 180 | Ala | Arg | Leu | Arg | Glu 185 | Asp | Glu | Gly | Cys | Ala 190 | Val | Ala | |
| GAG | CGG | CCG | CTG | CCC | CCG | CCC | TTT | GCG | CGT | CAG | CTC | TGG | CTG | CTC | TTC | 624 |
| Glu | Arg | Pro 195 | Leu | Pro | Pro | Pro | Phe 200 | Ala | Arg | Gln | Leu | Trp 205 | Leu | Leu | Phe | |
| GAA | TTT | CCT | GAG | AGC | TCG | CAG | GCT | GCG | CGC | GTG | CTC | GCC | GTG | GTC | TCC | 672 |
| Glu | Phe 210 | Pro | Glu | Ser | Ser | Gln 215 | Ala | Ala | Arg | Val | Leu 220 | Ala | Val | Val | Ser | |
| GTA | CTC | GTC | ATC | CTG | GTC | TCC | ATC | GTG | GTC | TTT | TGC | CTC | GAG | ACA | CTG | 720 |
| Val 225 | Leu | Val | Ile | Leu | Val 230 | Ser | Ile | Val | Val | Phe 235 | Cys | Leu | Glu | Thr | Leu 240 | |
| CCA | GAC | TTC | CGC | GAC | GAC | CGC | GAT | GAC | CCG | GGG | CTC | GCG | CCG | GTA | GCG | 768 |
| Pro | Asp | Phe | Arg | Asp 245 | Asp | Arg | Asp | Asp | Pro 250 | Gly | Leu | Ala | Pro | Val 255 | Ala | |
| GCT | GCT | ACT | GGC | TCG | TTC | CTC | GCT | CGG | CTC | AAT | GGC | TCC | AGT | CCC | ATG | 816 |
| Ala | Ala | Thr | Gly 260 | Ser | Phe | Leu | Ala | Arg 265 | Leu | Asn | Gly | Ser | Ser 270 | Pro | Met | |
| CCA | GGA | GCC | CCT | CCC | CGA | CAG | CCC | TTC | AAC | GAT | CCA | TTC | TTT | GTG | GTG | 864 |
| Pro | Gly | Ala 275 | Pro | Pro | Arg | Gln | Pro 280 | Phe | Asn | Asp | Pro | Phe 285 | Phe | Val | Val | |
| GAG | ACC | CTG | TGT | ATC | TGC | TGG | TTC | TCC | TTT | GAG | CTG | CTG | GTG | CAT | CTG | 912 |
| Glu | Thr | Leu 290 | Cys | Ile | Cys | Trp 295 | Phe | Ser | Phe | Glu | Leu 300 | Leu | Val | His | Leu | |
| GTG | GCC | TGC | CCT | AGC | AAA | GCT | GTG | TTC | TTC | AAG | AAT | GTG | ATG | AAC | CTA | 960 |
| Val 305 | Ala | Cys | Pro | Ser | Lys 310 | Ala | Val | Phe | Phe | Lys 315 | Asn | Val | Met | Asn | Leu 320 | |
| ATT | GAC | TTC | GTG | GCC | ATC | CTG | CCT | TAC | TTC | GTG | GCC | CTG | GGC | ACG | GAG | 1008 |
| Ile | Asp | Phe | Val | Ala 325 | Ile | Leu | Pro | Tyr | Phe 330 | Val | Ala | Leu | Gly | Thr 335 | Glu | |
| TTA | GCC | CGG | CAG | CGG | GGT | GTG | GGC | CAG | CCG | GCT | ATG | TCC | CTG | GCC | ATC | 1056 |
| Leu | Ala | Arg | Gln 340 | Arg | Gly | Val | Gly | Gln 345 | Pro | Ala | Met | Ser | Leu 350 | Ala | Ile | |
| CTA | AGG | GTC | ATC | CGA | TTG | GTG | CGT | GTC | TTC | CGC | ATC | TTC | AAG | CTC | TCC | 1104 |
| Leu | Arg | Val 355 | Ile | Arg | Leu | Val | Arg 360 | Val | Phe | Arg | Ile | Phe 365 | Lys | Leu | Ser | |
| AGG | CAT | TCG | AAG | GGT | CTA | CAG | ATC | TTG | GGT | CAG | ACA | CTG | CGG | GCT | TCC | 1152 |
| Arg | His | Ser 370 | Lys | Gly | Leu | Gln 375 | Ile | Leu | Gly | Gln | Thr 380 | Leu | Arg | Ala | Ser | |
| ATG | CGT | GAG | CTA | GGT | CTC | CTC | ATC | TCC | TTC | CTC | TTC | ATT | GGC | GTG | GTC | 1200 |
| Met | Arg 385 | Glu | Leu | Gly | Leu 390 | Leu | Ile | Ser | Phe | Leu 395 | Phe | Ile | Gly | Val | Val 400 | |
| CTC | TTT | TCC | AGC | GCA | GTC | TAC | TTT | GCT | GAA | GTG | GAC | CGG | GTG | GAC | ACC | 1248 |
| Leu | Phe | Ser | Ser | Ala 405 | Val | Tyr | Phe | Ala | Glu 410 | Val | Asp | Arg | Val | Asp 415 | Thr | |
| CAT | TTC | ACC | AGC | ATC | CCG | GAG | TCC | TTT | TGG | TGG | GCA | GTG | GTC | ACC | ATG | 1296 |
| His | Phe | Thr | Ser 420 | Ile | Pro | Glu | Ser | Phe 425 | Trp | Trp | Ala | Val | Val 430 | Thr | Met | |

-continued

| | | | | | | | | | | | | | | | | |
|---|---|---|---|---|---|---|---|---|---|---|---|---|---|---|---|---|
| ACC | ACG | GTT | GGC | TAT | GGG | GAC | ATG | GCA | CCC | GTC | ACC | GTG | GGT | GGC | AAG | 1344 |
| Thr | Thr | Val 435 | Gly | Tyr | Gly | Asp | Met 440 | Ala | Pro | Val | Thr | Val 445 | Gly | Gly | Lys | |
| ATC | GTG | GGC | TCT | CTG | TGT | GCC | ATT | GCA | GGT | GTG | CTC | ACC | ATC | TCT | CTG | 1392 |
| Ile | Val 450 | Gly | Ser | Leu | Cys | Ala | Ile 455 | Ala | Gly | Val | Leu | Thr 460 | Ile | Ser | Leu | |
| CCT | GTG | CCT | GTC | ATT | GTC | TCT | AAC | TTT | AGC | TAC | TTT | TAC | CAC | CGG | GAG | 1440 |
| Pro 465 | Val | Pro | Val | Ile | Val 470 | Ser | Asn | Phe | Ser | Tyr 475 | Phe | Tyr | His | Arg | Glu 480 | |
| ACA | GAG | GGC | GAA | GAG | GCA | GGG | ATG | TAC | AGC | CAT | GTG | GAC | ACA | CAG | CCC | 1488 |
| Thr | Glu | Gly | Glu | Glu 485 | Ala | Gly | Met | Tyr | Ser 490 | His | Val | Asp | Thr | Gln 495 | Pro | |
| TGC | GGT | ACC | CTG | GAG | GGC | AAG | GCT | AAT | GGG | GGG | CTG | GTG | GAC | TCT | GAG | 1536 |
| Cys | Gly | Thr | Leu 500 | Glu | Gly | Lys | Ala | Asn 505 | Gly | Gly | Leu | Val | Asp 510 | Ser | Glu | |
| GTG | CCT | GAA | CTC | CTC | CCA | CCA | CTC | TGG | CCC | CCT | GCA | GGG | AAA | CAC | ATG | 1584 |
| Val | Pro | Glu 515 | Leu | Leu | Pro | Pro | Leu 520 | Trp | Pro | Pro | Ala | Gly 525 | Lys | His | Met | |
| GTG | ACT | GAG | GTG | TGA | | | | | | | | | | | | 1599 |
| Val | Thr | Glu 530 | Val | | | | | | | | | | | | | |

( 2 ) INFORMATION FOR SEQ ID NO:10:

( i ) SEQUENCE CHARACTERISTICS:
( A ) LENGTH: 532 amino acids
( B ) TYPE: amino acid
( D ) TOPOLOGY: linear ( i i ) MOLECULE TYPE: protein ( x i ) SEQUENCE DESCRIPTION: SEQ ID NO:10:

| | | | | | | | | | | | | | | | |
|---|---|---|---|---|---|---|---|---|---|---|---|---|---|---|---|
| Met 1 | Thr | Thr | Arg | Glu 5 | Ser | Ser | Arg | Asp | Pro 10 | Arg | Lys | Ser | Ala | Gly 15 | Trp |
| Gln | Cys | Phe | His 20 | Arg | Cys | Gly | Thr | Ala 25 | Glu | Gly | Ala | Pro | Ser 30 | Pro | Ala |
| Gly | Val | Thr 35 | Pro | Pro | Pro | Pro | Arg 40 | Pro | Gly | Arg | Thr | Phe 45 | His | Ala | |
| Ile | Phe 50 | Thr | Arg | Arg | His | Arg 55 | Thr | Pro | Asp | Trp | Gly 60 | Gly | Cys | Gly | Val |
| Gly 65 | Ala | Thr | Arg | Pro | Phe 70 | Thr | Gly | Arg | Pro | Cys 75 | Ala | Arg | His | Gly 80 | |
| Ala | Thr | Val | Pro | Ala 85 | Ala | Leu | Arg | Cys | Cys 90 | Glu | Arg | Leu | Val | Leu 95 | Asn |
| Val | Ala | Gly | Leu 100 | Arg | Phe | Glu | Thr | Arg 105 | Ala | Arg | Thr | Leu | Gly 110 | Arg | Phe |
| Pro | Asp | Thr 115 | Leu | Leu | Gly | Asp | Pro 120 | Val | Arg | Arg | Ser | Arg 125 | Phe | Tyr | Asp |
| Gly | Ala 130 | Arg | Ala | Glu | Tyr | Phe 135 | Phe | Asp | Arg | His | Arg 140 | Pro | Ser | Phe | Asp |
| Ala 145 | Val | Leu | Tyr | Tyr | Tyr 150 | Gln | Ser | Gly | Gly | Arg 155 | Leu | Arg | Arg | Pro | Ala 160 |
| His | Val | Pro | Leu | Asp 165 | Val | Phe | Leu | Glu | Glu 170 | Val | Ser | Phe | Tyr | Gly 175 | Leu |
| Gly | Arg | Arg | Leu 180 | Ala | Arg | Leu | Arg | Glu 185 | Asp | Glu | Gly | Cys | Ala 190 | Val | Ala |
| Glu | Arg | Pro 195 | Leu | Pro | Pro | Pro | Phe 200 | Ala | Arg | Gln | Leu | Trp 205 | Leu | Leu | Phe |
| Glu | Phe | Pro | Glu | Ser | Ser | Gln | Ala | Ala | Arg | Val | Leu | Ala | Val | Val | Ser |

|   |   |   |   |   | 210 |   |   |   |   | 215 |   |   |   |   | 220 |   |   |   |   |
|---|---|---|---|---|---|---|---|---|---|---|---|---|---|---|---|---|---|---|---|

Val Leu Val Ile Leu Val Ser Ile Val Val Phe Cys Leu Glu Thr Leu
225                     230                 235                 240

Pro Asp Phe Arg Asp Asp Arg Asp Asp Pro Gly Leu Ala Pro Val Ala
                245                 250                 255

Ala Ala Thr Gly Ser Phe Leu Ala Arg Leu Asn Gly Ser Ser Pro Met
            260                 265                 270

Pro Gly Ala Pro Pro Arg Gln Pro Phe Asn Asp Pro Phe Phe Val Val
            275                 280                 285

Glu Thr Leu Cys Ile Cys Trp Phe Ser Phe Glu Leu Leu Val His Leu
        290             295                 300

Val Ala Cys Pro Ser Lys Ala Val Phe Phe Lys Asn Val Met Asn Leu
305                 310                 315                 320

Ile Asp Phe Val Ala Ile Leu Pro Tyr Phe Val Ala Leu Gly Thr Glu
                325                 330                 335

Leu Ala Arg Gln Arg Gly Val Gly Gln Pro Ala Met Ser Leu Ala Ile
            340                 345                 350

Leu Arg Val Ile Arg Leu Val Arg Val Phe Arg Ile Phe Lys Leu Ser
            355                 360                 365

Arg His Ser Lys Gly Leu Gln Ile Leu Gly Gln Thr Leu Arg Ala Ser
370                 375                 380

Met Arg Glu Leu Gly Leu Leu Ile Ser Phe Leu Phe Ile Gly Val Val
385                 390                 395                 400

Leu Phe Ser Ser Ala Val Tyr Phe Ala Glu Val Asp Arg Val Asp Thr
                405                 410                 415

His Phe Thr Ser Ile Pro Glu Ser Phe Trp Trp Ala Val Val Thr Met
            420                 425                 430

Thr Thr Val Gly Tyr Gly Asp Met Ala Pro Val Thr Val Gly Gly Lys
        435                 440                 445

Ile Val Gly Ser Leu Cys Ala Ile Ala Gly Val Leu Thr Ile Ser Leu
    450                 455                 460

Pro Val Pro Val Ile Val Ser Asn Phe Ser Tyr Phe Tyr His Arg Glu
465                 470                 475                 480

Thr Glu Gly Glu Glu Ala Gly Met Tyr Ser His Val Asp Thr Gln Pro
            485                 490                 495

Cys Gly Thr Leu Glu Gly Lys Ala Asn Gly Gly Leu Val Asp Ser Glu
        500                 505                 510

Val Pro Glu Leu Leu Pro Pro Leu Trp Pro Pro Ala Gly Lys His Met
    515                 520                 525

Val Thr Glu Val
    530

( 2 ) INFORMATION FOR SEQ ID NO:11:

( i ) SEQUENCE CHARACTERISTICS:
   ( A ) LENGTH: 30 base pairs
   ( B ) TYPE: nucleic acid
   ( C ) STRANDEDNESS: double
   ( D ) TOPOLOGY: both ( x i ) SEQUENCE DESCRIPTION: SEQ ID NO:11:

CTATTTTTAC GNGCGGACAC CGGACTACCG        30

( 2 ) INFORMATION FOR SEQ ID NO:12:

( i ) SEQUENCE CHARACTERISTICS:
   ( A ) LENGTH: 17 base pairs (B) TYPE: nucleic acid
(C) STRANDEDNESS: double
(D) TOPOLOGY: both (xi) SEQUENCE DESCRIPTION: SEQ ID NO:12:

GGCTGGGGCG GCGGNGG                                                                                  17

(2) INFORMATION FOR SEQ ID NO:13:

(i) SEQUENCE CHARACTERISTICS:
(A) LENGTH: 69 base pairs
(B) TYPE: nucleic acid
(C) STRANDEDNESS: double
(D) TOPOLOGY: both (xi) SEQUENCE DESCRIPTION: SEQ ID NO:13:

TGCTCGTCCG TAGTCTCCGT GCTCCTCATC CTCGTCTCCA TCGTCGTCTT CTGCCTCGAG    60

ACGCTGCCT                                                           69

(2) INFORMATION FOR SEQ ID NO:14:

(i) SEQUENCE CHARACTERISTICS:
(A) LENGTH: 27 base pairs
(B) TYPE: nucleic acid
(C) STRANDEDNESS: double
(D) TOPOLOGY: both (xi) SEQUENCE DESCRIPTION: SEQ ID NO:14:

CCCGACTCCG CTGAATGGCT CCCAGCC                                       27

(2) INFORMATION FOR SEQ ID NO:15:

(i) SEQUENCE CHARACTERISTICS:
(A) LENGTH: 23 base pairs
(B) TYPE: nucleic acid
(C) STRANDEDNESS: double
(D) TOPOLOGY: both (xi) SEQUENCE DESCRIPTION: SEQ ID NO:15:

ATTCTTTGTG GTGGAACCTT TGT                                           23

(2) INFORMATION FOR SEQ ID NO:16:

(i) SEQUENCE CHARACTERISTICS:
(A) LENGTH: 93 base pairs
(B) TYPE: nucleic acid
(C) STRANDEDNESS: double
(D) TOPOLOGY: both (xi) SEQUENCE DESCRIPTION: SEQ ID NO:16:

ATCTGCTGGT TCTCCTTTGA GCATGCTGGT GCGTCTGGCG GCGTGTCCAA GCAAAGCTGT    60

ATTTTTCAAG AATGTGATGA ACCTTATTGA CTT                                93

(2) INFORMATION FOR SEQ ID NO:17:

(i) SEQUENCE CHARACTERISTICS:
(A) LENGTH: 45 base pairs
(B) TYPE: nucleic acid
(C) STRANDEDNESS: double
(D) TOPOLOGY: both (xi) SEQUENCE DESCRIPTION: SEQ ID NO:17:

GTGGCCATCC TGCCTTACTT TGTGGCCCTG GGCACAGAGT TAGCC                   45

(2) INFORMATION FOR SEQ ID NO:18:

( i ) SEQUENCE CHARACTERISTICS:
  ( A ) LENGTH: 196 base pairs
  ( B ) TYPE: nucleic acid
  ( C ) STRANDEDNESS: double
  ( D ) TOPOLOGY: both ( x i ) SEQUENCE DESCRIPTION: SEQ ID NO:18:

| | | | | | | |
|---|---|---|---|---|---|---|
| GTCAGCGGGG | CGTGGGCCAG | CCAGCTATGT | CCCTGGCCAT | CCTGAGGAGT | CATCNGATTG | 60 |
| GTGCGTAGTC | TTCCGCATCT | TCAAGCTNTC | CNGGCANTCN | AAGGGCNTGC | AAATCTTGGG | 120 |
| CCAGGACGCT | TCGGGCCTCC | ATGCGTGAAG | CTGGGCCTCC | TCATCTTTTT | CCTCTTCATC | 180 |
| GGTGTGGTCC | TCTTTT | | | | | 196 |

( 2 ) INFORMATION FOR SEQ ID NO:19:

( i ) SEQUENCE CHARACTERISTICS:
  ( A ) LENGTH: 271 base pairs
  ( B ) TYPE: nucleic acid
  ( C ) STRANDEDNESS: double
  ( D ) TOPOLOGY: both ( x i ) SEQUENCE DESCRIPTION: SEQ ID NO:19:

| | | | | | | |
|---|---|---|---|---|---|---|
| TTTCCCTGCC | AGTGCCCGTC | ATTGTCTCCA | ATTTCAGCTA | CTTTTATCAC | CGGGAGACAG | 60 |
| AGGGCGAAGA | GGCTGGGATG | TTCAGCCATG | TGGACATGCA | GCCTTGTGGC | CCACTGGANG | 120 |
| GNNCANGNCN | ANNCCAATGG | GGGGCTGGTG | GACGGGGAGG | TACCTGAGCT | ACCACCTCCA | 180 |
| CTCTGGGCAC | CCCCAGGGAA | ACACCTGGTC | ACCGAAGTGT | GAGGAACAGT | TGAGGTCTGC | 240 |
| AGGAATTCGA | TATCAAGCTT | ATCGATACCG | T | | | 271 |

( 2 ) INFORMATION FOR SEQ ID NO:20:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:20:

| | | |
|---|---|---|
| TCTCCGTACT | CGTCATCCTG | G | 21 |

( 2 ) INFORMATION FOR SEQ ID NO:21:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:21:

| | | |
|---|---|---|
| AAATGGGTGT | CCACCCGGTC | | 20 |

VOLTAGE-GATED POTASSIUM CHANNEL GENE, KV1.7, VECTORS AND HOST CELLS COMPRISING THE SAME, AND RECOMBINANT METHODS OF MAKING POTASSIUM CHANNEL PROTEINS

CROSS-REFERENCE TO RELATED APPLICATIONS

This is a continuation-in-part of U.S. application Ser. No. 08/207,401, filed Mar. 4, 1994, abandoned.

Reference is hereby made to the following related applications: Ser. No. 07/955,916, filed Oct. 2, 1992, now U.S. Pat. No. 5,372,702, and Ser. No. 08/170,418, filed Dec. 20, 1993, and to their parent applications, all of which being hereby expressly incorporated by reference.

FIELD OF THE INVENTION

The present invention relates to the identification of a new voltage-gated potassium channel gene, Kv1.7, which is expressed in the rat and hamster insulinoma cell lines, RINm5F and HIT, respectively. Since voltage-gated potassium channels modulate insulin secretion from pancreatic β-cells, selective Kv1.7 blockers would be expected to increase insulin release and thereby reduce hyperglycemia associated with non-insulin-dependent diabetes mellitus.

The present invention is also directed toward assays for testing extrinsic materials for their ability to block the Kv1.7 channel, and thereby exert an effect on insulin secretion from β-cells. To this end, we have generated an expression construct, containing the coding region of the Kv1.7 gene and have demonstrated that this gene, when expressed in Xenopus oocytes, encodes a voltage-dependent, rapidly-activating, non-inactivating delayed rectifier-type channel that is both tetraethylammonium- and 4-aminopyridine-resistant. This construct can now be used for the development of mammalian cell lines expressing this channel; such cell lines could be used in high-throughput screening assays of extrinsic materials.

BACKGROUND OF THE INVENTION

Mammalian cell membranes perform very important functions relating to the structural integrity and activity of various cells and tissues. Of particular interest in membrane physiology is the study of trans-membrane ion channels which act to directly control a variety of physiological, pharmacological and cellular processes. Numerous ion channels have been identified including calcium (Ca), sodium (Na) and potassium (K) channels, each of which have been analyzed in detail to determine their roles in physiological processes in vertebrate and insect cells.

A great deal of attention has recently been focused on the potassium channel because of its involvement in maintaining normal cellular homeostasis. A number of these potassium channels open in response to changes in the cell membrane potential. Many voltage-gated potassium channels have been identified and are distinguishable based on their electrophysiological and pharmacological properties. An extended family of at least twenty genes have been isolated, each encoding functionally distinct voltage-gated potassium channels, and each with a unique tissue distribution pattern. Several of these have been shown to be involved in maintaining the cell membrane potential and controlling the repolarization of the action potential in neurons, muscle and pancreatic β-cells. Potassium currents have been shown to be more diverse than sodium or calcium currents and also play a role in determining the way a cell responds to an external stimulus. The diversity of potassium channels and their important physiological role highlights their potential as targets for developing therapeutic agents for various diseases.

Type II or non-insulin-dependent diabetes (NIDDM) is a chronic and debilitating disorder affecting at least 5% of the human population (Bell, G. I. et al., 1980, *Nature* 284:26 and Horst-Sikorska, W. et al., 1994, *Hum. Genet.* 93:325). NIDDM, manifested as fasting hyperglycemia, results either from a defect in insulin release from pancreatic β-cells or from the inability of peripheral tissues to respond appropriately to insulin (Bell, G. I. et al., 1980, supra, Horst-Sikorska, W. et al., 1994, supra and Herman, W. H. et al., 1994, *Diabetes* 43:40).

Current therapeutic management of this disease is based primarily on the use of drugs (sulfonylurea compounds) that enhance insulin release by selectively modulating $K_{ATP}$ channels (Boyd III, A. E., 1988, *Diabetes* 37:847, Rajan, A. S. et al., 1990, *Diabetes Care* 13:340, Misler, S. et al., 1986, *Proc. Natl. Acad. Sci USA* 83:7119, Petersen, O. H. and Findlay, I., 1987, *Physiol. Rev.* 67:1054 and Ashcroft, F. M., 1988, *Ann. Rev. Neurosci.* 11:97). Hypoglycemia is a frequent side effect of such anti-diabetic therapy because these drugs, mimicking the action of glucose, induce membrane depolarization of β-cells (Bell, G. I. et al., 1980, supra, Horst-Sikorska, W. et al., 1994, supra and Herman, W. H. et al., 1994, supra, Boyd III, A. E., 1988, supra, Rajan, A. S. et al., 1990, supra, Misler, S. et al., 1986, supra, Petersen, O. H. and Findlay, I., 1987, supra, Ashcroft, F. M., 1988, supra, Dukes, I. et al., 1994, *J. Biol. Chem.* 269:10979, Cook, D. L. et al., 1991, *Trends Neurosci.* 14:411, Smith, P. A. et al., 1990, *J. Gen. Physiol.* 95:1041, Smith, P. A. et al., 1990, *FEBS Lett.* 261:187, Atwater, I. et al., 1983, *Cell Calcium* 4:451, Ammala, C. et al., 1991, *Nature* 353:849 and Worley III, J. F. et al., 1994, *J. Biol. Chem.* 269:12359). Sulfonylurea-induced insulin release, therefore, occurs in a glucose-independent manner. A glucose-dependent insulin secretagogue could potentially avoid the debilitating side effect of hypoglycemia, and would therefore be extremely useful.

Another form of treatment in severe long-standing NIDDM is insulin replacement. This approach, although effective, is time-consuming, expensive and requires the administration of painful injections often many times daily. To say the least, NIDDM patients would welcome a more effective treatment with fewer side effects. An understanding of the mechanisms responsible for insulin secretion may help identify new targets for the development of such novel anti-diabetic drugs.

Transmembrane ion channels are the primary elements that transduce signals in pancreatic β-cells, resulting in the release of insulin (Boyd III, A. E., 1988, supra, Rajan, A. S. et al., 1990, supra, Misler, S. et al., 1986, supra, Petersen, O. H. and Findlay, I., 1987, supra, Ashcroft, F. M., 1988, supra, Dukes, I. et al., 1994, supra, Cook, D. L. et al., 1991, supra, Smith, P. A. et al., 1990, *J. Gen. Physiol.* 95:1041, Smith, P. A. et al., 1990, *FEBS Lett.* 261:187, Atwater, I. et al., 1983, supra, Ammala, C. et al., 1991, supra and Worley III, J. F. et al., 1994, supra.). In response to an elevation in external glucose, the β-cell membrane slowly depolarizes (phase I). This metabolic coupling appears to be due to an increase in cytosolic ATP, which results in the closure of ATP-sensitive potassium ($K_{ATP}$) channels. The membrane depolarization in turn initiates sinusoidal bursts of calcium action potentials (phase II), during which intracellular calcium rises, triggering insulin secretion (Boyd III, A. E., 1988, supra, Rajan, A.

S. et al., 1990, supra, Misler, S. et al., 1986, supra, Petersen, O. H. and Findlay, I., 1987, supra, Ashcroft, F. M., 1988, supra, Dukes, I. et al., 1994, supra, Cook, D. L. et al., 1991, supra, Smith, P. A. et al., 1990, *J. Gen. Physiol.* 95:1041, Smith, P. A. et al., 1990, *FEBS Lett.* 261:187, Atwater, I. et al., 1983, supra, Ammala, C. et al., 1991, supra and Worley III, J. F. et al., 1994, supra). Voltage-gated potassium channels have been suggested to play a critical role in repolarizing the membrane after each of these calcium spikes.

Alteration in any of these ionic signalling events could interfere with insulin release and result in hyperglycemia. Overexpression of voltage-gated potassium channels, for example, might be expected to excessively hyperpolarize the membrane following each calcium spike and thereby inhibit the reopening of voltage-gated calcium channels with the reduction in calcium entry leading to diminished insulin release and hyperglycemia. We have therefore focused our attention on identifying the pancreatic islet cell voltage-gated potassium channel.

SUMMARY OF THE INVENTION

The present invention relates to the identification of a new voltage-gated potassium channel gene, Kv1.7, which is expressed in the rat and hamster insulinoma cell lines, RINm5F and HIT, respectively. Thus, the present invention is predicated on the identification and characterization of a marker molecule in pancreatic β-cells that modulates insulin release and that leads to a general therapeutic target for NIDDM. This predicate, in combination with the generation of an expression construct, makes possible the development of an assay to identify extrinsic materials possessing the ability to selectively modulate the marker and thereby modulate insulin secretion.

Having established a link between potassium channel function and insulin secretion from pancreatic β-cells as a predicate of the present invention, it follows that the present invention is further directed to associated consequential aspects including assays for testing extrinsic materials for their ability to modulate the Kv1.7 potassium channel, and thereby exert an effect on insulin secretion from pancreatic β-cells.

The present invention is further directed to a method for treating NIDDM in an organism manifesting said disease comprising contacting said organism with an extrinsic material having a modulating effect on Kv1.7 potassium channels, such materials identified by employing the assay system described supra.

The present invention is further directed to kits containing the associated structure, reagents and means to conduct screening assays as described supra.

Further, the present invention is directed to the foregoing aspects in all their associated embodiments as will be represented as equivalents within the skill of those in the art.

The present invention is thus directed to the management and control of NIDDM including selectively screening for, preferably selective, modulators of Kv1.7 potassium channels for use as a therapeutic.

BRIEF DESCRIPTION OF THE FIGURES

FIG. 1A represents the mouse Kv1.7 coding sequence which is indicated by the two stippled boxes. The six bars within these regions indicate the putative membrane-spanning domains S1 through S6. Restriction sites are indicated as follows: BglII (B), EcoRI (E), PstI (P) and SacI (S). The order of restriction sites was determined by single, partial and double digests and by DNA sequencing. Also indicated is a comparison of the genomic sequence of mouse Kv1.7 (SEQ ID NOS: 1 and 3) with that of mouse (mKv1.7) (SEQ ID NO: 5) and hamster (haKv1.7) (SEQ ID NO: 7) cDNAs showing the splice donor and acceptor sites which form the boundaries of the single intervening sequence.

FIG. 1B shows the deduced amino acid sequence (SEQ ID NO:10) of mouse Kv1.7. The six putative membrane-spanning domains (S1 through S6) and pore-forming region (P) are also indicated. Potential sites of post-translational modification are shown as follows: N-glycosylation (*); tyrosine kinase (TY-K) and protein kinase C (PKC). Every tenth residue is indicated by a dot above. The hydrophobic core of this protein shares considerable sequence similarity with other Shaker-family channels, while the intracellular N- and C-termini and the external loops between S1/S2 and S3/S4 show little conservation.

FIG. 2 shows Northern blot analysis of total RNA isolated from the hamster insulinoma HIT cell line (H) and rat insulinoma RINm5F cell line (R). The probe used was a PstI/SacI fragment from the Kv1.7-specific 3' untranslated region of the Kv1.7 cDNA. Molecular weight markers are also presented. In both cases a 2.0 kilobase band is observed.

FIGS. 3A, 3B and 3C present the complete nucleotide sequence (SEQ ID NO:9) of the entire coding region for the mouse Kv1.7 gene as compared to portions of the human Kv1.7 gene sequence(SEQ ID NOS:11–19). The mouse Kv1.7 (SEQ ID NO:9) sequence is presented on the top line whereas the bottom line represents the corresponding human Kv1.7 sequence (SEQ ID NOS:11–19). Dashes (-) in the human sequence represent nucleotides that are identical to those presented in the mouse sequence. Open spaces in the human sequence represent regions for which no sequence data is available.

FIG. 4 shows the deduced order of two potassium channel genes, hKv1.7 and hKv3.3, on human chromosome 19.

DETAILED DESCRIPTION OF THE INVENTION

A. Definitions

By the term "extrinsic material" herein is meant any entity that is not ordinarily present or functional with respect to the Kv1.7 potassium channel and/or pancreatic islet cells and that affects the same. Thus, the term has a functional definition and includes known, and particularly, unknown entities that are identified to have a modulating effect on Kv1.7 channel expression, and/or the associated pancreatic islet cells.

By the term "modulating effect", or grammatical equivalents, herein is meant both active and passive impact on the Kv1.7 potassium channel and/or pancreatic islet cells. These include, but shall not be construed as limited to, blocking or activating the channel or the function of the channel protein to materials that ordinarily permeate therethrough, reducing or increasing the number of ion channels per cell and use of secondary cell(s) or channel(s) to impact on a primary abnormal cell.

B. Detailed Description

A new Shaker-related potassium channel gene. We now have identified a novel potassium channel gene, Kv1.7, which belongs to the Shaker-subfamily of genes. A restriction map of a 6.4 kilobase EcoRI DNA fragment containing the entire mouse Kv1.7 coding region is shown in FIG. 1A.

Unlike all other known mammalian Shaker-related genes (Kv1.1–Kv1.6) that have intronless coding regions (Swanson, R. A. et al., 1990, *Neuron* 4:929, Chandy, K. G. et al., 1990, *Science* 247:973, Douglass, J. et al., 1990, *J. Immunol.* 144:4841, Roberds, S. L. and Tamkun, M. M., 1991, *Proc. Natl. Acad. Sci. USA* 88:1798, Tamkun, M. M. et al., 1991, *FASEB J.* 5:331, Migeon, M. B. et al., 1992, *Epilepsy Res.* 6(supp.):173 and Shelton, P. A. et al., 1993, *Receptors and Ion Channels* 1:25), the protein coding region of mouse Kv1.7 is interrupted by a single 1.9 kilobase intron whose splice sites are shown in FIG. 1A. The deduced mouse Kv1.7 protein (SEQ ID NO:10) consists of 532 amino acids and contains six putative membrane-spanning domains, S1–S6 (FIG. 1B). The upstream exon encodes the amino terminus and the first transmembrane segment (S1), while the remainder of the coding sequence is contained within the downstream exon.

Expression of Kv1. 7 in pancreatic β-cells. Northern blot assays using a Kv1.7-specific 3'-NCR probe revealed a strongly hybridizing 2 kilobase band in the rat and hamster insulinoma lines, RINm5F and HIT (see FIG. 2). RINm5F and HIT cells are neoplastic versions of pancreatic β-cells and can secrete insulin in response to glucose challenge like their normal counterparts. These cells have been widely used as models for normal pancreatic β-cells. We have also demonstrated the presence of Kv1.7 mRNAs in these cells by PCR analysis, which we confirmed by sequencing (a portion of the hamster sequence is shown in FIG. 1). Betsholtz, C. et al., 1990, *FEBS Lett.* 263:121 have also used PCR to amplify a short segment of Kv1.7 cDNA spanning the S5/S6 region from mouse (MK-6), rat (RK-6) and hamster (HaK-6) insulin-producing cells. Our sequence is identical to their MK-6 sequence in the short region of overlap, except for four single nucleotide changes.

These results led us to hypothesize that Kv1.7 is expressed in normal pancreatic islet β-cells, and may play an important role in the electrical events regulating insulin release, making it a potential therapeutic target for NIDDM. To test this idea, we provided Kv1.7-specific DNA probes to Dr. Julie Tseng-Crank at Glaxo, for in situ hybridization on histological sections of pancreata from normal and diabetic db/db mice. In confirmation of our prediction, Dr. Tseng-Crank found that Kv1.7 mRNA was present in both normal and diabetic islet cells.

Electrophysiological and pharmacological properties of Kv1.7. To study the properties of this channel, we generated an expression construct in which the intron was spliced out, along with the 5'- and 3'-non-coding sequences. This construct, when expressed in Xenopus oocytes, encodes a channel which is voltage-dependent, rapidly-activating and non-inactivating, and is TEA- and 4AP-resistant.

Chromosomal location of Kv1.7 in humans. DNA probes from mouse Kv1.7 and Kv3.3 were isolated and sent to the Human Genome (Chromosome 19) Center at Lawrence Livermore laboratory. We had previously demonstrated that Kv1.7 and Kv3.3 were located on human chromosome 19 (Ghanshani, S. et al., 1992, Genomics 12:190 and McPherson et al., 1991, in Eleventh International Workshop on Human Gene Mapping), and needed more specific localization. Dr. Mohrenweiser's group used these mouse probes to isolate human Kv1.7- and Kv3.3containing cosmid clones from a chromosome 19 library, and then used the human cosmids as fluorescent-probes for in situ hybridization experiments to map both genes to human 19q13.3-13.4. The idiogram of human chromosome 19 shown in FIG. 4 indicates that Kv1.7 (KCNA7) is located centromeric of Kv3.3 (KCNC3). Genes for both glycogen synthase (GSY) and the histidine-rich calcium protein (HRC) also map centromeric of Kv3.3, but the order of Kv1.7, HRC and GSY could not be resolved by fluorescence in situ hybridization experiments. Studies by S. Elbein and colleagues, however, have placed HRC approximately 4 cM centromeric to GSY.

NIDDM is heterogeneous in its etiology, and families have been described in which the disease is associated with mutations in either glucokinase (chromosome 7) or a gene closely linked to adenosine deaminase (chromosome 20) (Vaxillaire, M. et al., 1994, *Diabetes* 43:389, Froguel, P. et al., 1993, *N. Eng. J. Med.* 328:697 and Bell, G. I. et al., 1991, *Proc. Natl. Acad. Sci. USA* 88:1484). Additional forms of NIDDM exist which are not linked to either of these genes (Vaxillaire, M. et al., 1994, supra, Froguel, P. et al., 1993, supra and Bell, G. I. et al., 1991, supra) and recent studies suggest that a locus predisposing to diabetes exists at human chromosome 19q13.3. First, in a large group of unrelated patients in Finland, a polymorphism of the GSY gene is associated with the development and severity of NIDDM (Groop, L. C. et al., 1993, *N. Eng. J. Med.* 328:10 and Vestergaard, et al., 1993, *J. Clin. Invest.* 91:2342). However, there was no evidence for structural defects in the GSY gene or alterations in the total level of GSY protein in these patients, indicating that expression of this gene was unaltered, and suggesting that GSY may only be a marker for another gene on 19q13.3 (Groop, L. C. et al., 1993, supra and Vestergaard, et al., 1993, supra). More recent studies using polymorphic markers in this region exclude the GSY gene as a candidate (Vaxillaire, M. et al., 1994, supra, Froguel, P. et al., 1993, supra, Bell, G. I. et al., 1991, supra, Groop, L. C. et al., 1993, supra and Vestergaard, et al., 1993, supra), and suggest that a diabetic susceptibility gene may lie centromeric to HRC and away from GSY. The localization of the islet cell potassium channel gene, Kv1.7 (KCNA7), to human 19q13.3 and its overexpression in diabetic islets therefore make it a candidate; Kv1.5 was excluded because it is on human chromosome 12p13 (Curren, M. et al., 1992, *Genomics* 12:729 and Attali, B. et al., 1993, *J. Biol. Chem.* 268:24283), and is not found in islet cells (see above). Thus, Kv1.7 may be a candidate gene for some inherited forms of NIDDM associated with impaired insulin secretion.

Sequence analysis of the human Kv1.7 gene. Numerous partial human Kv1.7 cDNA clones have been isolated using the mouse Kv1.7 cDNA as a probe and sequence data from the human Kv1.7 gene have been obtained. Partial human Kv1.7 sequences, (SEQ ID NOS:11–19) in comparison to the sequences of the mouse Kv1.7 coding region, (SEQ ID NO:9) is shown in FIGS. 3A and 3B. The sequence information in FIGS. 3A and 3B demonstrates that portions of the human Kv1.7 gene possess a great deal of homology with that of the mouse Kv1.7 gene.

Kv1.7-selective blockers could function as glucose-dependent insulin secretagogues. We have shown that Kv1.7 is a novel Shaker-related gene encoding a rapidly activating, non-inactivating, TEA-resistant voltage-gated potassium channel expressed in pancreatic β-cells. Voltage-gated potassium channels with properties similar to Kv1.7 have been reported to regulate membrane repolarization following each calcium spike during phase II of insulin secretion. A Kv1.7 blocker would therefore be expected to lead to glucose-dependent modulation of insulin release, potentially avoiding the debilitating side effect of hypoglycemia. Such drugs would have wide therapeutic use in the management of NIDDM.

Use of the Kv1.7 expression construct to identify Kv1.7-specific glucose-dependent insulin secretagogues. The Kv1.7 expression construct described above has been successfully used to generate functional potassium channels with unique properties. This construct or related ones can be used for expression of functional Kv1.7 channels in mammalian cell lines that do not express endogenous potassium channels (e.g., CV-1, NIH-3T3, or RBL cell lines). These cell lines can then be loaded with $^{86}$Rb (Rb ions permeate through potassium channels nearly as well as potassium ions) in the presence of absence of extrinsic materials, and Kv1.7 modifiers identified by their ability to alter $^{86}$Rb-efflux. When natural toxins are identified which block Kv1.7 activity, modifiers of Kv1.7 activity could also be identified by their ability to block or reverse the binding of labeled toxins to cells expressing this channel. Compounds discovered in either of these manners could then be formulated and administered as therapeutic agents for the treatment of NIDDM.

C. Materials and Methods

1. Screening of the Mouse Genomic DNA Library

To isolate the Kv1.7 cDNA, approximately $5\times10^5$ plaques from an AJR/J mouse genomic library were screened (genomic DNA partially digested with the restriction endonuclease Mbo I and cloned into the vector J1, a derivative of L47.1) (a gift of Jonathan Kaye, University of California, San Diego, La Jolla, Calif.). The genomic library was screened using a mixture of the mouse Kvl.1 (MK1) (Temple et al., *Nature* 332:837 (1988)) and rat Kvl.5 (KV1) cDNA (Swanson et al., *Nature* 332:837 (1990)) as a probe. Probes were labeled with $^{32}P$ to a specific activity of $1\times10^9$ cpm/ug by the random primer method of Feinberg and Vogelstein, *Anal. Biochem.* 132:6 (1983). The mouse Kvl.1 (MK1) cDNA probe containing the entire 1485 base pair coding region was obtained from Bruce Tempel (University of Washington, Seattle, Wash.). The 1.1 kilobase fragment probe derived from the rat Kvl.5 (KV1) cDNA, containing the coding region from S3 to its end, was obtained from Leonard Kaczmarek (Yale University, New Haven, Conn.). Hybridization was performed at 55° C. in hybridization buffer for 16–18 hr. Hybridization buffer consists of 5×SSC, 10× Denhardt's (0.2% bovine serum albumin, 0.2% polyvinyl pyrrolidone), and 0.1% SDS. The blots were washed at a final stringency of 0.5×SSC and 0.1% SDS for 60 min at 55° C. The blots were then exposed to X-OMAT AR film (Kodak, Rochester, N.Y.) at –70 ° C. using an intensifying screen.

DNA was isolated from positive phage clones, digested to completion with HindIII and electrophoresed on a 0.9% agarose gel. DNA was transferred to nitrocellulose membranes by capillary transfer and Southern blotting was performed by the method of Southern, *Methods in Enzymology* (R. Wu, Ed.), 68:152, Academic Press, New York. Hybridizing and non-hybridizing fragments were then subcloned into the HindIII site of the pUC19 plasmid vector.

2. Restriction Mapping

To generate a restriction map of the DNA inserts, plasmid DNA was digested with from 1–3 restriction enzymes and the order of restriction fragments assembled from the results. The insert DNA was then sequenced by the dideoxynucleotide termination method (Sanger et al., *Proc. Natl. Acad. Sci. USA* 74:5463 (1977)) and the resultant genomic sequence was aligned with that of the Shaker-related mouse Kvl.1 (MK1) cDNA. For Southern blotting experiments, digested DNA fragments were separated by electrophoresis on a 0.9% agarose gel and then electrotransfered to Nylon membrane (Nytran, Schleicher & Schuell, Keen, N.H.) using 1× Tris-acetate/EDTA transfer buffer. Electrotransfer was carried out at 4° C. for 14 hrs at 100 mA. Hybridization and washing were carried out using the same reagents and conditions described above for the library screening. Exposure of the blots was done on X-OMAT film (Kodak, Rochester, N.Y.) at room temperature for 30 minutes.

3. DNA Sequencing

A fragment containing a majority of the coding region was cloned into pBluescript (Stratagene, La Jolla, Calif.), and the inserts were sequenced by the dideoxynucleotide chain termination method (Sanger et al., *Proc. Natl. Acad. Sci. USA* 74:5463 (1977)) using modified T7 DNA polymerase (Sequenase; US Biochemicals, Cleveland, Ohio). Plasmid-specific primers and custom designed oligonucleotide primers (purchased from Chemgenes, Needham, Mass.) were used for this purpose.

4. Northern Blots

For Northern blot analysis, total RNA was isolated by the guanidine thiocyanate method (Chirgwin et al., *Biochemistry* 18:5294 (1979)) using the RNAgents™ total RNA isolation kit (Promega, Madison, Wis.). Ten nanograms of total RNA was fractionated on a 1% agarose gel after denaturation with glyoxal and dimethyl sulfoxide (McMaster and Carmichael, *Proc. Natl. Acad. Sci. USA* 74:4835 (1977)) and was transferred by the capillary method to nylon membrane (Vrati et al., *Mol. Biol. Rep.(Bio-Rad Laboratories)* 1(3):1 (1987)).

A PstI/SacI fragment from the Kv1.7-specific 3' untranslated region of the cDNA clone was radioactively labeled by the random primer method to a specific activity of $1\times10^9$ cpm/microgram and used as a probe. Hybridization was performed at 55° C. in hybridization buffer consisting of 5×SSC, 10' Denhardt's and 0.1% SDS. The blot was then washed at a final stringency of 0.5×SSC and 0.1% SDS for 30 minutes at 55 ° C. and then exposed to X-OMAT film for 72 h at –70 ° C. with an intensifying screen.

5. Polymerase Chain Reaction

Total RNA isolated from mouse brain and from the hamster insulinoma cell line, HIT-TI5, was used to generate random primed cDNA by the method of Krug and Berger, *Methods in Enzymology* (S. L. Berger and A. R. Kimmel, Eds.) 152:316 (1987) Academic Press, San Diego. The 40 microliter reaction mixture contained 40 units of avian myeloblastosis virus reverse transcriptase (Promega, Madison, Wis.), 20 units of RNasin (Promega, Madison, Wis.), 100 pM random hexanucleotide triphosphate (GeneAmp kit; Perkin-Elmer-Cetus, Norwalk, Conn.). The cDNA product was then amplified for 25 cycles with an annealing temperature of 57 ° C. with TaqI polymerase (Promega, Madison, Wisconsin) using two oligonucleotide primers derived from the sequence of the mouse Kv1.7 genomic clone. The upstream primer 5'-TCTCCGTACTCGTCATCCTGG- 3' (SEQ ID NO:20) corresponds to sequence in the S1 transmembrane segment and the downstream primer 5'-AAATGGGTGTCCACCCGGTC- 3'(SEQ ID NO:21) corresponds to the 3'–>5' complementary sequence of the carboxy terminus of the S3—S4 loop of mouse Kv1.7. The reaction mixture contained 60 mM Tris-HCl pH 8.5, 25 mM $(NH_4)_2SO_4$, 2.5 mM $MgCl_2$, 10% dimethyl sulfoxide, 0.25 microgram of each primer, 2.5 mM of each deoxynucleotide triphosphate and 5 units of TaqI polymerase (Mullis et al., *Cold Spring Harbor Symp. Quant. Biol.* 51:263 (1986)).

6. Human Chromosome Localization

Mouse genomic Kv1.7 DNA was used to isolate a human Kv1.7 cosmid clone from a human chromosome 19-enriched library (Library F) (de Jong et al., *Cytogen. Cell Genet.* 51:985 (1989)), containing an approximately 4× coverage of chromosome 19 as described by Tynan et al., *Nucl. Acids Res.* 20:1629 (1992) and Tynan et al., *Genomics* 17:316

(1993). The probe insert fragment was isolated and labeled by random priming (Feinberg and Vogelstein, *Anal. Biochem.* 132:6 (1983)) with $^{32}$P-dCTP for probing. Fluorescence in situ hybridization (FISH) of cosmids to metaphase chromosomes was performed as previously described by Trask, *Methods Cell Biol.* 35:3 (1990) and Trask et al., *Genomics* 15:133 (1993). Two color hybridization to metaphase chromosomes was performed as described by Brandriff et al., *Genomics* 12:773 (1992).

7. Expression Construct

A mouse Kv1.7 expression construct was generated by combining genomic sequences with PCR-derived cDNA sequences in the pBluescript vector, and cRNA was prepared and injected into Xenopus oocytes as described by Aiyar et al., 1993, *Amer. J. Physiol.* 265:C1571.

8. Materials Testing

The Kv1.7 expression construct described above or related ones expressing the Kv1.7 potassium channel gene can be used to generate functional potassium channels in mammalian cell lines that do not express endogenous potassium channels by transfection of the construct into the cell line. These cell lines are then loaded with $^{86}$Rb ions which permeate through potassium channels nearly as well as potassium ions. The loaded cells can then be cultured in the presence or absence of extrinsic materials and Kv1.7 channel blockers are identified by their ability to prevent $^{86}$Rb-efflux. The methods for the above experiments are all well known in the art.

9. Preparation of antibodies against the Kv1.7 potassium channels

The gene encoding the Kv1.7 potassium channel are isolated by standard recombinant DNA techniques such as described in Weir et al., Handbook of Experimental Immunology, Vol. 3 (1986) and other available documents. These genes are used as templates to prepare Kv1.7 potassium channel proteins or peptides, which are used as antigens to prepare antibodies against the Kv1.7 potassium channel. A second method for preparing antibodies against the Kv1.7 potassium channel protein is used with cells expressing large numbers of the Kv1.7 channel, isolating the cell surface proteins from these cells and using these proteins as antigens for the preparation of antibodies. The antibodies are then screened for the ability to effect Kv1.7 potassium channels electrophysiologically.

10. Drug and/or antibody testing in Type II diabetes mellitus

Materials comprising drugs or antibodies identified by assays designed to identify extrinsic materials possessing the ability to modulate the Kv1.7 potassium channel may be tested in vivo for efficacy in appropriate animal models, for example, for their ability to treat NIDDM by increasing secretion of insulin from pancreatic β-cells. The route of administration of the drugs/antibodies can be oral, parental, or via the rectum, and the drug could be administered alone as principals, or in combination with other drugs or antibodies, and at regular intervals or as a single bolus, or as a continuous infusion in standard formations. Drugs or antibodies described supra are also tested in in vitro assays, for example, for their ability to stimulate secretion of insulin from pancreatic β-cells derived from patients or animal models of NIDDM.

11. A treatment protocol

Candidate materials identified by the assays described above are tested for safety in humans as per Federal guidelines. These candidates described supra are administered via standard formulations to diseased patients, again either orally, parenterally, rectally, alone or in combination, at regular intervals or as a single bolus, or as a continuous infusion, for modulating Kv1.7 potassium channels in pancreatic β-cells, thereby impacting on the course of the disease.

The foregoing description details specific methods that can be employed to practice the present invention. Having detailed specific methods initially used to identify extrinsic materials possessing the ability to modulate the Kv1.7 potassium channels on pancreatic β-cells, one skilled in the art will well enough know how to devise alternative reliable methods for arriving at the same basic information and for extending this information to other species including humans. Thus, however detailed the foregoing may appear in text, it should not be construed as limiting the overall scope hereof; rather, the ambit of the present invention is to be governed only by the lawful construction of the appended claims.

What is claimed is:

1. An isolated DNA molecule encoding a Kv1.7 potassium channel protein having the amino acid sequence shown in SEQ ID NO: 10.

2. A DNA molecule according to claim 1, having the nucleotide sequence shown in SEQ ID NO: 9.

3. A replicable vector comprising a DNA molecule according to claim 1,

4. A vector according to claim 3, wherein said vector is an expression vector.

5. A cultured cell comprising heterologous DNA having the sequence of the DNA molecule of claim 1.

6. A cell according to claim 5, wherein said cell is a mammalian cell.

7. A method of producing a Kv1.7 potassium channel protein comprising the steps of introducing a DNA molecule according to claim 1 into a suitable expression system and effecting the expression of said molecule, whereby said potassium channel protein is produced.

* * * * *